United States Patent [19]

Bakas et al.

[11] Patent Number: 4,870,222
[45] Date of Patent: Sep. 26, 1989

[54] ALKYLATION/TRANSALKYLATION PROCESS

[75] Inventors: Steve T. Bakas, Woodridge; Paul T. Barger, Arlington Heights, both of Ill.

[73] Assignee: UOP, Des Plaines, Ill.

[21] Appl. No.: 266,040

[22] Filed: Nov. 2, 1988

Related U.S. Application Data

[63] Continuation-in-part of Ser. No. 124,147, Nov. 23, 1987, Pat. No. 4,826,801, which is a continuation-in-part of Ser. No. 932,113, Nov. 18, 1986, Pat. No. 4,735,929, which is a continuation-in-part of Ser. No. 772,099, Sep. 3, 1985, abandoned.

[51] Int. Cl.⁴ ............................................. C07C 2/00
[52] U.S. Cl. ................................... 585/323; 585/467; 585/474
[58] Field of Search ........................................ 585/323

[56] References Cited

U.S. PATENT DOCUMENTS

| | | | |
|---|---|---|---|
| 2,419,599 | 4/1947 | Schulze | 260/671 |
| 2,848,514 | 8/1958 | de Keizer et al. | 260/671 |
| 3,751,504 | 8/1973 | Keown et al. | 260/672 T |
| 3,803,255 | 4/1974 | Ellis et al. | 260/671 P |
| 4,335,022 | 6/1982 | Slaugh | 252/455 R |
| 4,459,426 | 7/1984 | Inwood et al. | 585/323 |

Primary Examiner—Curtis R. Davis
Attorney, Agent, or Firm—Thomas K. McBride; John F. Spears, Jr.

[57] ABSTRACT

A process for the production of a monoalkylated aromatic compound which minimizes the production of undesirable alkylating agent oligomers, while producing monoalkylaromatics in high yields. The process entails the combination of an alkylation reaction zone, a separations zone, and a transalkylation reaction zone wherein the alkylation catalyst and transalkylation catalyst are dissimilar and where the alkylation catalyst is comprised of noncrystaline silica-alumina material and the transalkylation catalyst is comprised of an acid-modified crystalline aluminosilicate material that is characterized as having a surface area of at least 580 m²/g following acid washing after catalyst particle formulation.

17 Claims, 2 Drawing Sheets

ALKYLATION/TRANSALKYLATION PROCESS

CROSS-REFERENCE TO RELATED APPLICATIONS

This application is a continuation-in-part of prior copending application Ser. No. 124,147 filed Nov. 23, 1987, now U.S. Pat. No. 4,826,801 which is a continuation-in-part of application Ser. No. 932,113 filed Nov. 18, 1986, now U.S. Pat. Mo. 4,735,929, which is a continuation-in-part of application Ser. No. 772,099 filed Sept. 3, 1985, now abandoned, the contents of which are incorporated herein by reference thereto.

BACKGROUND OF THE INVENTION

The present invention is related to an improved alkylation/transalkylation process which utilizes a dual reactor system employing dissimilar catalysts to produce a monoalkylaromatic product. More specifically, this invention involves the use of a noncrystalline (also known as amorphous) silica-alumina material to catalyze the alkylation reaction, and an inorganic oxide bound crystalline aluminosilica material acid treated after formulation into a catalyst particle to catalyze the transalkylation reaction. The invention also relies upon a synergism of the two reaction zones and a separations zone to produce a high purity monoalkylated aromatic product while producing negligible amounts of undesirable product poisons and heavy by-products.

The alkylation of aromatics with an alkylating agent in the presence of an alkylating reactant is a process well known for its ability to produce such monoalkylaromatic products as ethylbenzene, cumene, linear alkylbenzenes and so forth. Such monoalkylaromatic compounds are important chemical precursors in the production of detergents and polymers among others. Alkylation catalysts that are known to produce alkylaromatic compounds include the well known Friedel-Crafts catalysts; sulfuric acid, phosphoric acid, hydrofluoric acid, and aluminum chloride in either liquid or solid supported form. Solid granular catalysts such as clays, zeolites, and amorphous materials have also been utilized as alkylating reactants in both a modified and naturally occurring form.

The use of a transalkylation reaction zone in conjunction with an alkylation reaction zone for the production of monoalkylaromatics is also well known. A transalkylation reaction zone employed in a process in conjunction with an alkylation reaction zone enables the alkylation reaction zone to be operated at higher conversion conditions due to the ability of the transalkylation reactant to convert the undesired polyalkylaromatic compounds produced by the higher alkylation zone conversion conditions into desired monoalkylaromatic compounds. Translakylation catalysts that are known to have utility in the production of alkylaromatics from polyalkylaromatics include Friedel-Crafts catalysts such as sulfuric acid, phosphoric acid, aluminum chloride in either the liquid or solid supported form, and the like. Solid granular catalysts such as clays, zeolites, and amorphous materials have also been utilized as transalkylation reactants.

A myriad of processing schemes employing an alkylation reaction zone, a transalkylation reaction zone, and a separations zone, and employing various product, feed, and intermediate product recycles are well known to produce monoalkylaromatic products in high yields. One drawback concerning existing alkylation/transalkylation processes is the potential for the alkylation and/or the transalkylation catalyst to produce undesirable products such as alkylting agent oligomers, heavy polyaromatic compounds, and unwanted monoalkylaromatics. The alkylating agent oligomers can be especially troublesome as they re often recovered with the desired monoalkylaromatic product where they can detrimentally affect the utility of the monoalkylaromatic product in further conversion processes. An example of this would be the contamination of cumene with propylene oligomers which may reduce the utility of using such contaminated cumene as a phenol process feedstock and ultimately for the production of phenolic resins due to the presence of the oligomers as an inert compound within the cross-linked resins.

Another drawback inherent to some existing alkylation/transalkylation processes is the use of Friedel-Crafts catalysts such as solid phosphoric acid or hydrofluoric acid as the alkylation and/or transalkylation catalysts. Many of these catalysts require a water cofeed and produce an extremely corrosive sludge by-product. The utilization of such sludge-producing catalysts in an alkylation process requires that special design considerations be made regarding unit metallurgy, safety, and by-product neutralization. Such design considerations are typically costly and may add significantly to the construction and operations costs of such processes. Additionally, the use of Friedel-Crafts catalysts requires a once-through processing scheme to ensure that damaging corrosive materials are not recycled into the reaction zone. This requirement necessitates the operation of the process at high conversion conditions which tend to produce greater amounts of unwanted by-products such as alkylating agent oligomers and heavy by-products.

SUMMARY OF THE INVENTION

A new process which employs an alkylation reaction zone, a separations zone, and a transalkylation zone, and which utilizes an amorphous silicaalumina alkylation catalyst and an acid-washed crystalline aluminosilicate transalkylation catalyst has been surprisingly found to have utility in producing a monoalkylaromatic compound in very high yields. Additionally, it has been discovered that the product from the process above contains amounts of alkylating oligomers that are much lower than those observed in a conventional solid acid alkylation process. In fact in some cases, the levels of alkylating agent oligomers is below that able to be detected by conventional analytical techniques. Finally, the catalysts that have been surprisingly found to produce the best results in the above alkylation/transalkylation process possess the additional advantage of not being corrosive and therefore do not require the special design considerations which must be afforded an acidic catalyst such as solid phosphoric acid.

In one of its broad aspects, the present invention embodies an improved alkylation/transalkylation process which comprises a unique combination of an alkylation reaction zone containing a noncrystalline silicaalumina alkylation catalyst, a transalkylation reaction zone containing an acid-washed crystalline aluminosilicate transalkylation catalyst, and a separations section wherein an alkylating agent and an aromatic substrate are reacted to produce a monoalkylaromatic product. The separations zone is characterized in that it separates as fractions: (1) the unreacted aromatic substrate for use as a portion of the alkylation reaction zone and/or transalkylation reaction zone feed, (2) polyalkylated aromatic compounds for use as a portion of the transalkylation zone reactor feed, and (3) a monoalkylaromatic compound which is recovered as the desired product. An undesired product stream comprising hydrocarbon compounds that are lower in molecular weight than the aromatic substrate is recovered in the separations section as is an undesired hydrocarbon product stream comprised of compounds with a higher molecular weight than the polyalkylaromatic compounds.

Additionally, as part of the broad embodiment of the instant invention, a portion of the alkylation reaction zone product stream may be recycled to the inlet of the alkylation reaction zone as a portion of the alkylation reaction zone feed. Finally, it is a further objective of this invention to utilize as the alkylation reaction zone catalyst a noncrystalline silica-alumina catalyst, and to use as the transalkylation reaction zone catalyst, an acid-modified inorganic oxide bound crystalline aluminosilicate catalyst. Additionally, it should be noted that the alkylating agent employed in the process can consist of an alkene, an alcohol, an alkylhalide, an alkylsulfonate, or mixtures thereof where the carbon number of the alkylating agent ranges from 2-18.

In a more specific embodiment, this invention relates to a process for the production of isopropylbenzene hereinafter referred to as cumene from the alkylation reaction of the aromatic substrate benzene with the alkylating agent propylene. The alkylation reaction takes place in an alkylation reaction zone containing a catalyst comprised of a noncrystalline silica-alumina material which has a $SiO_2/Al_2O_3$ ratio of from 2:3 to 99:1 where the catalyst exists as spheres, extrudates, or granular particles. The alkylation reaction zone is further characterized by its ability to accept as a feed portion, a recycled portion of the alkylation reaction zone product stream and a recycled portion of the unreacted aromatic substrate which has been recovered in the separations zone. Liquid fractions comprising a portion to all of the alkylation reaction zone product stream along with the entire transalkylation reaction zone product stream are directed to the separations zone for separation into fractions comprising a benzene-rich fraction, a cumene fraction, and a fraction comprising polyisopropylbenzene compounds. The transalkylation reaction zone contains a crystalline silica-alumina catalyst in the form of spheres, extrudates, or granular particles. The transalkylation reaction zone catalyst preferably comprises hydrogen form mordenite, bound with an inorganic oxide. The support is contacted with an acidic aqueous solution after it is formed. The acidic contacting occurs at conditions selected to increase the surface area of the composite to at least 580 $m^2/g$ without increasing the silica/alumina ratio of the mordenite. The transalkylation zone feed is comprised of a portion of the separated unreacted benzene fraction and the separated polyisopropylbenzene compounds of which a portion to all of the unreacted benzene fraction has been recovered in the separations section. These, as well as other embodiments of the present invention will become evident from the following, more detailed description.

INFORMATION DISCLOSURE

Prior alkylation art discloses many different catalysts and process configurations employing alkylation and transalkylation reaction zones for the production of monoalkylated aromatics. The use of silica-alumina catalysts that are in a crystalline and noncrystalline form as an alkylation and/or transalkylation catalysts is well known. That the modification of catalysts with an acid base, or a common chemical compound can improve catalyst performance in some hydrocarbon reaction processes is also known.

A great many of the prior art cases describing an alkylation/transalkylation process specify the use of the same catalyst in both reaction zones. This is the case in U.S. Pat. No. 4,459,426 (Inwood et al) which describes a process that is configured very much like that of the present invention except that it clearly dictates the use of a steam stabilized hydrogen Y-zeolite as the alkylation and transalkylation reaction zone catalyst. U.S. Pat. No. 3,751,504 (Keown et al) discloses the use of a crystalline aluminosilica catalyst in both the alkylation and transalkylation reaction zones of an aromatic alkylation process. The process configuration disclosed and the fact that the process entails a gas phase reaction are areas where the '504 process differs from the process of the present invention.

Fewer prior art disclosures teach the merits of using dissimilar catalysts in the alkylation and transalkylation zones of an aromatic alkylation process. One in particular, U.S. Pat. No. 3,551,510 (Pollitzer et al), teaches of the use of a solid phosphoric acid catalyst in the alkylation zone, and of the use of a hot hydrochloric acid extracted mordenite catalyst in the transalkylation zone. U.S. Pat. No. 3,551,510 is very similar to the present invention, however it does not support the use of a silica-alumina catalyst in the alkylation zone. As a result, it does not discover the benefits of such a catalyst for producing an alkylation reaction product stream with a low concentration of alkylating agent oligomers as measured by bromine index.

The use of a noncrystalline silica-alumina catalyst to reduce the acid wash color of an alkylated aromatic product is disclosed in U.S. Pat. No. 3,803,255 (Ellis et al). The acid wash color described in the aforementioned invention is a measure of functional impurities such as olefins and oxygenated compounds recovered in the product. This is similar but not the same as the bromine index which was mentioned previously. This same prior art disclosure further supports the use of either a crystalline or noncrystalline silica-alumina material in a reaction zone directly following the alkylation reaction zone where essentially no alkylation takes place due to a lack of an olefin alkylating agent but where the acid wash color of the product is improved. Another invention which describes the use of a noncrystalline silica-alumina material in an alkylation reaction zone is U.S. Pat. No. 2,848,514 (de Keizer at al) which discloses the use of a cracking catalyst comprised of from 70–90 wt. % of $SiO_2$ and of 10–30 wt. % of $Al_2O_3$ in an alkylation zone but where the desired product is diisopropylbenzene.

The use of an alumina modified silica in an alkylation reaction zone is claimed in U.S. Pat. No. 4,335,022 (Slaugh) and also in U.S. Pat. No. 2,419,599 (Schulze). Both references teach of the benefits of using an alumina exchanged noncrystalline silica as an alkylation catalyst. The Schulze reference further limits the amount of alumina used to less than 2 wt. % while the Slaugh invention is proported to be an improvement over a conventional silica-alumina catalyst similar to that utilized in the alkylation zone of the present invention.

The prior art recognizes a myriad of catalyst formulations for the alkylation or transalkylation of hydrocarbons. It is well known that acids, such as strong mineral acids, can be used to modify crystalline aluminosilicate zeolite powders through decationization and dealumination. Ammonium compounds have also been successfully employed to convert crystalline aluminosilicates from alkali and/or alkaline metal cation form to the hydrogen form. Combinations of zeolite and refractory inorganic oxide have been disclosed, however, the art is silent as to the inherent problem of loss of the zeolite surface area as a result of dilution and forming techniques associated with the refractory inorganic oxide.

Combinations of the acid and ammonium treatments have been disclosed for use on aluminosilicate powders. U.S. Pat. No. 3,475,345 (Benesi) discloses a method of converting aluminosilicate zeolites, particularly a sodium form synthetic mordenite, to the hydrogen form utilizing a three-step pretreatment performed on the powdered zeolite. These pretreatment steps consist of: (1) a hot acid treatment, (2) a cold acid treatment, and (3) treatment with an ammonium compound. U.S. Pat. No. 3,442,794 (Van Heiden et al) also discloses a method for the pretreatment of aluminosilicate zeolites to the hydrogen form. Again, the preferred zeolite is the synthetic sodium form of mordenite. The method disclosed is very similar to U.S. Pat. No. 3,475,345 mentioned above, with the distinguishing feature being a separately performed two-step pretreatment with (1) an acid compound and (2) an ammonium compound in arbitrary order. An important feature of both references is that the treatments are performed solely on the aluminosilicate zeolite with the express intention of modifying said zeolite before being utilized in a catalyst formulation and that no mention of the importance of the surface area of the catalytic composite is disclosed. This is distinguished from the present invention in that any treatment performed is subsequent to the zeolite being incorporated into a formed catalyst composite and more importantly without any apparent modification of the zeolite itself.

Treatment of the aluminosilicates with acid have not only been effective for conversion to the hydrogen form, but also have been used as a means for increasing the silica-to-alumina ratio. Typically, a silica-to-alumina ratio of about 10:1 is observed for a sodium form synthetic mordenite and is substantially unchanged if an ammonium treatment is used to convert the mordenite to the hydrogen form. If a mordenite powder is subjected to an acid treatment as taught in U.S. Pat. No. 3,597,155 (Flanigen), an increase in the silica-to-alumina ratio is effected. The acid treatment is believed to cause a reduction of the frame work tetrahedra aluminum atoms, thus increasing the proportion of silicon atoms present in the zeolitic structure.

U.S. Pat. No. 3,562,345 (Mitsche) discloses the use of a crystalline aluminosilica material as a transalkylation catalyst characterized in that the material has a pore diameter of from 3 to 8 angstroms, and a $SiO_2/Al_2O_3$ mole ratio of from 6 to 12, where the crystalline aluminosilica material is mordenite. The disclosure is however silent to the benefits of acid modification of the material to improve its utility in a transalkylation reaction zone. As mentioned previously, U.S. Pat. No. 3,551,510 describes an alkylation/transalkylation process which utilizes a hydrochloric acid-modified mordenite as the transalkylation zone catalyst. This catalyst is similar to the transalkylation catalyst of the present invention which is an acid-washed mordenite containing catalyst. The prior art case however discloses its use in conjunction with a solid phosphoric acid alkylation catalyst in a process where there is no separations zone between the alkylation and transalkylation reaction zones. Additionally, the mordenite component of the transalkylation catalyst of U.S. Pat. No. 3,551,510 is acid-washed in pure form to such an extent that some alumina is actually leached from the mordenite. This is distinguished from the transalkylation catalyst of the instant invention which is acid-washed in a finished form only to clear debris that may be plugging the catalyst pores.

A common attribute of the above-mentioned prior art is that, in all cases, the crystalline aluminosilicate alone, in particular the synthetic sodium form of mordenite, is subjected to an acid and/or an ammonium pretreatment step(s) to modify the aluminosilicate before its incorporation into the catalyst composition. Although the pretreatment of mordenite as described in the above references enhances the performance of catalytic composites comprising such pretreated mordenite, further improvements are still obtainable.

The unique process combination disclosed in the present invention has surprisingly been found to have great utility in the production of a monoalkylaromatic compound from a feed comprising an aromatic compound and an alkylating agent where the desired monoalkylaromatic product is produced in high yields while undesired alkylating agent oligomers and heavy by-products are produced in unexpectedly negligible amounts.

DETAILED DESCRIPTION

It is the object of the present invention to provide a new process for the production of alkylated aromatics in high yields wherein the desired product is produced through the synergism of an alkylation reaction zone containing an alkylation reaction catalyst, a transalkylation reaction zone containing a transalkylation catalyst and a separations zone which unites the two reaction zones to create a continuous process.

The first step of the process of the present invention comprises passing an admixture of an alkylating agent and an aromatic substrate into an alkylation reaction zone containing an alkylation catalyst. The alkylating agent which may be charged to the alkylation reaction zone may be selected from a group of diverse materials including monoolefins, diolefins, polyolefins, acetylenic hydrocarbons, and also alkylhalides, alcohols, ethers, esters, the later including the alkylsulfates, alkylphosphates and various esters of carboxylic acids. The preferred olefin-acting compounds are olefinic hydrocarbons which comprise monoolefins containing one double bond per molecule. Monoolefins which may be utilized as olefin-acting compounds in the process of the present invention are either normally gaseous or normally liquid at standard conditions, and include ethylene, propylene, 1-butene, 2-butene, isobutylene, and the higher molecular weight normally liquid olefins such as the various pentenes, hexenes, heptenes, octenes, and mixtures thereof, and still higher molecular weight liquie olefins, the latter including various olefin polymers having from about 9 to about 18 carbon atoms per molecule including propylene trimer, propylene tetramer, propylene pentamer, etc. Cycloolefins such as cyclopentene, methylcyclopentene, cyclohexane, methylcyclohexene, etc., may also be utilized, although not necessarily with equivalent results.

It is a preferred embodiment of the present invention that the monoolefin contains at least 2 and not more than 15 carbon atoms. More specifically, it is preferred that the monoolefin is propylene.

The aromatic substrate of the present invention which is charged to alkylation reaction zone in admixture with the alkylating agent may be selected from a group of aromatic compounds which include individually and in admixture with benzene and monocyclic alkyl-substituted benzene of from 7 to 12 carbon atoms having the structure:

where R is methyl, ethyl or a combination thereof, and n is an integer from 1 to 5. In other words, the aromatic substrate portion of the feedstock may be benzene, benzene containing from 1 to 5 methyl and/or ethyl group substitutents, and mixtures thereof. Non-limiting examples of such feedstock compounds include benzene, toluene, xylene, ethylbenzene, mesitylene (1,3,5-trimethylbenzene) and mixtures thereof. It is specifically preferred that the aromatic substrate is benzene.

The alkylation reaction zone catalyst of the process of this invention may be any solid or liquid catalyst known in the prior art. The most preferred alkylation reaction zone catalyst of the present invention is comprised of a noncrystalline, also known as amorphous, silica-alumina material. The catalyst may be prepared from amorphous silica and alumina in a soluble gel form, in a colloidal form, as a precipitate, or in any other form such that the silica, the alumina, and the combination is in a noncrystalline or amorphous form. The alkylation reaction zone catalyst may be manufactured as particles, spheres, or extrudates. It is preferred that the alkylation reaction zone catalyst of the present invention is spherical.

In a preferred method of preparation, the alkylation reaction zone catalyst of the present invention is a cogelled silica-alumina material. The silicaalumina composite utilized herein is synthetically prepared and is considered to function as the catalytic element of the final catalyst composite. In accordance with the present invention, the cogelled silica-alumina composite comprises from about 40 to about 99 wt. % silica and from about 1 to about 60 wt. % alumina.

The cogelled silica-alumina composition is suitably prepared as spheroidal particles by the well-known oil drop method. In a preferred method of manufacture, an alumina sol, utilized as an alumina source, is commingled with an acidified water glass solution as a silica source, and the mixture is further commingled with a suitable gelling agent, for example, urea, hexamethylenetetramine (HMT), or mixtures thereof. The mixture is discharged while still below gelation temperature by means of a nozzle or rotating disk, into a hot oil bath maintained at or above gelation temperature. The mixture is dispersed into the hot oil bath as droplets which form into spherical gel particles. The alumin sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are aged, usually in the oil bath, for a period of at least 10–16 hours, and then in a suitable alkaline or basic medium for at least 3 to about 10 hours, and finally water washed. Proper gelation of the mixture in the oil bath, as well as subsequent aging of the gel spheres, is not readily accomplished below about 50° C., and at about 100° C., the rapid evolution of the gases tend to rupture and otherwise weaken the spheres. By maintaining sufficient superatmospheric pressure during the forming and aging steps in order to maintain water in the liquid phase, a higher aging temperature may be employed, frequently with improved results. If the gel particles are aged at superatmospheric pressure, no alkaline aging step is required.

The spheres are water-washed, preferably with water containing a small amount of ammonium hydroxide and/or ammonium nitrate. After washing, the spheres are dried, at a temperature from about 95°–250° C. for a period from about 6 to about 24 hours or more, and then calcined at a temperature from about 300°–760° C. for a period from about 2 to about 12 hours or more.

In a continuous process for alkylating aromatic hydrocarbons with olefins, the previously described reactants are continuously fed into a pressure vessel containing the above described noncrystalline silica-alumina catalyst. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably from about 2:1 to 8:1. The preferred molar feed ratios help to maximize the catalyst life cycle by minimizing the deactivation of the catalyst by coke and heavy hydrocarbon deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor.

In some cases, in order to maintain the reaction temperature in the preferred range and thus reduce the formation of unwanted polyalkylaromatics, it may be desired to quench the reactants to dissipate heat of reaction. A quench stream comprised of the alkylating agent olefin, or a portion of the alkylation reactor effluent or mixtures thereof may be injected into the alkylation reactor system in order to dissipate heat and supply additional amounts of olefin alkylating agent and unreacted aromatic substrate at various locations within the reaction zone. This is accomplished for example in a single-stage reactor by multiple injection of the aforementioned quench steam components into the reaction zone via strategically placed inlet lines leading into said reaction zone. The amount and composition of quench material injected into either a single stage reaction system or multi-stage reaction system may be varied according to need. Benefits resulting from multiple quench injection include elimination of costly cooling apparatus in the process, improved selectivity to formation of the desired alkylaromatic compound, provision for a larger heat sink and optimization of the olefin to aromatic compound molar ratio throughout the reaction zone thus resulting in increased yield of the desired monoalkylated aromatic compound. Additionally, multiple injection of quench material improves catalyst life.

Temperatures which are suitable for use in the process herein are those temperatures which initiate a reaction between an aromatic substrate and the particular olefin used to selectively produce the desired monoalkylaromatic compound. Generally, temperatures suitable for use are from about 100° C. to about 390° C., especially from about 150° C. to about 275° C. Pressures which are suitable for use herein preferably are above about 1 atm but should not be in excess of about 130 atm. An especially desirable pressure range is from about 10 to about 40 atm; with a liquid hourly space velocity (LHSV) based upon the benzene feed rate of from about 0.5 to about 50 $hr^{-1}$, and especially from about 2 to about 10 $hr^{-1}$. It should be noted that the temperature and pressure combination used herein is to be such that the alkylation and transalkylation reactions take place in essentially the liquid phase. In a liquid phase proces for producing alkylaromatics, the catalyst is continuously washed with reactants, thus preventing buildup of coke precursors on the catalyst. This results in reduced amounts of carbon forming on said catalyst in which case catalyst cycle life is extended as compared to a gas phase alkylation process in which coke formation and catalyst deactivation is a major problem. To further reduce the rate of catalyst deactivation, it is contemplated that $H_2$ may be added to the alkylation reaction zone feed and the transalkylation reaction zone feed in an amount sufficient to saturate the respective reaction zone liquid feeds. The addition of $H_2$ in equilibrium amounts to the respective liquid phase feed streams helps to reduce the catalyst deactivation rate by inhibiting the polymerization potential of pore blocking polymerizable compounds produced by the process.

A substantial portion of the aromatic substrate hydrocarbon and essentially all of the olefin alkylating agent react in the alkylation reaction zone in the presence of the noncrystalline silica-alumina alkylation catalyst to form, in addition to the desired monoalkylaromatic compound, polyalkylaromatic compounds. These undesirable polyalkylaromatic hydrocarbons may contain two or more alkyl groups that have from 1 to 18 carbon atoms, for example, the di-, tri-, and tetraisopropylbenzene hydrocarbons. It is an important aspect of this invention to recover and transalkylate these polyalkylaromatic compounds in order to maximize the amount of the desired monoalkylaromatic hydrocarbons produced by the process.

The alkylation reaction zone product may be divided into two portions before entering the separations section. One portion may be transported to the inlet of the alkylation reactor and admixed with the alkylation reactor feed and/or used as all or a portion of a reaction zone quench stream as hereinbefore mentioned. Another portion may be directed to the separations zone. The portion that is directed to the inlet of the alkylation reaction zone is comprised of from 0 to 95 wt. % of the reactor effluent and preferably 50 to 90 wt. % of the reactor effluent. This alkylation reaction zone portion may be directed back to the alkylation reaction zone so that the process can be operated at a per-pass conversion rate that maximizes monoalkylaromatic production while keeping the separations zone equipment economically sized. The alkylation reaction zone product portion that is directed to the separations zone is comprised of the alkylation reactor effluent stream portion not being recycled to the alkylation reaction inlet. This alkylation reaction zone product portion is separated into at least three fractions using any conventional separation techniques available that will result in essentially pure fractions of (1) an aromatic substrate, (2) a monoalkylaromatic compound, and (3) a polyalkylated aromatic compound. An example of some of the separations techniques that could be employed alone or in combination in the separations zone to produce essentially pure fractions of the hereinbefore mentioned separations zone products are: distillation including vacuum, atmospheric, and superatmospheric distillation; extraction techniques including, for example, liquid/liquid extractions, vapor/liquid extractions, supercritical extractions and others; absorption techniques, adsorption techniques, and any other known mass transfer techniques which can achieve the recovery of the desired separations zone products in essentially pure fractions. The separation processes mentioned above are included as examples of the many techniques which could be utilized to achieve the necessary separation, purification and recovery of the alkylation and transalkylation reaction zone products. Hence, separations zone processing conditions are not disclosed as they will depend upon the choice of the separation techniques employed and further upon the configuration of the separations zone equipment. It is expected that continuous distillation will be the primary separations technique used in the separations zone. The optimal distillation conditions will again depend upon the exact scheme chosen to achieve the desired separation.

As previously mentioned, the transalkylation reaction zone product as will hereinafter be described is directed as a whole to the separations zone. Additionally, a portion to all of the fresh aromatic substrate feed stream may be directed initially to the separations zone. Directing the aromatic substrate feed to the separations zone enables the processing of aromatic substrate feedstocks which are comprised mainly of the desired aromatic substrate feed component but which may contain deleterious amounts of undesirable components. In directing the aromatic substrate feedstock, first to the separations section, an essentially pure aromatic substrate feed stream can be provided as a portion of the feedstock to both the alkylation reaction zone and transalkylation reaction zone from a previously contaminated aromatic substrate feedstock.

To reiterate, the separations zone product fractions are essentially pure streams of the desired monoalkylaromatic compound, the unreacted aromatic substrate feed compound, and the polyalkylated aromatic compounds. In addition, a separations zone product fraction comprised of hydrocarbon materials lower in molecular weight than the aromatic substrate feed compound is separated in the separations zone and recovered from the process as an undesirable product of the alkylation zone and transalkylation zone reactions. A final undesirable by-product fraction which is separated from the alkylation and transalkylation reaction products in the separations zone is comprised of all materials that have molecular weights higher than the heaviest polyalkylated aromatic compound. Fractions comprising the desired monoalkylaromatic product, the light hydrocarbon by-product materials, and heavy hydrocarbon by-product materials exit the process and are separately recovered. The fraction comprised of the aromatic feed substrate may be recycled in part to the alkylation reaction zone and in part to the transalkylation reaction zone. Normally, from about 25 wt. % to about 90 wt. %, and preferably from about 30 wt. % to about 85 wt. % of the aromatic substrate fraction is transported to the alkylation zone. The remainder of the aromatic substrate fraction and the entire polyalkylated aromatic fraction are transported to the transalkylation reaction zone as the transalkylation reaction zone feed.

The transalkylation reaction zone accepts as feed the entire polyalkylaromatic fraction and can accept as feed a portion of the aromatic substrate fraction recovered in the separations zone. A stream consisting of the aromatic substrate feed that has not been recovered in the separations zone but which has originated from a source outside of the process may be used as a portion of or all of the aromatic substrate feed being directed to the transalkylation reaction zone.

The polyalkylaromatic stream that is utilized as a portion of the transalkylation reaction zone feed is comprised of aromatic compounds which are characterized as constituting an aromatic substrate based molecule with two or more alkylating agent compounds taking the place of two or more hydrogen atoms around the aromatic substrate ring structure.

The transalkylation reaction zone is utilized to remove the alkylating agent compounds in excess of one from the ring structure of the polyalkylated aromatic compounds and to transfer the alkylating agent compound to an aromatic substrate molecule that has not been previously alkylated thus increasing the amount of monoalkylated aromatic compounds produced by the process. To transalkylate polyalkylaromatics with an aromatic substrate, a feed mixture containing an aromatic substrate and polyalkylated aromatic compounds in mole ratios ranging from 1:1 to 50:1 and preferably from 4:1 to 10:1 are continuously or intermittently introduced ito a transalkylation reaction zone containing a transalkylation catalyst at transalkylation conditions. The transalkylation catalyst that is utilized in the transalkylation reaction zone of the present invention is a crystalline aluminosilicate material and a refractory inorganic oxide material that has been acid-washed following formation into a catalytic particle. The catalyst is characterized as having an average pore diameter of 6 angstroms or greater, and a surface area of 580 $m^2/g$ or greater.

According to the present invention, there is provided a catalyst composition for the transalkylation of aromatic hydrocarbons. The transalkylation catalyst composition of the present invention comprises a hydrogen form mordenite and from about 0.5 to 50 wt. % alumina, and preferably 5 to 25 wt. % alumina with said catalyst composition having a surface area of at least 580 $m^2/g$. We have found that significant improvements in transalkylation performance are realized when the surface area of the catalyst composition is at or above 580 $m^2/g$. Although a maximum surface area of the catalyst composition has not been determined experimentally, it is believed that an upper limit of 700 $m^2/g$ is possible. Obtaining such a high surface area in the range from about 580 to 700 $m^2/g$ is the object of one of the embodiments of the subject invention and is further illustrated in subsequent examples.

An essential component of the instant invention is the hydrogen form mordenite. While mordenite is naturally occurring, a variety of synthetic mordenites are available commercially, usually in a powder form. These synthetic mordenites can be obtained in both the sodium form and hydrogen form and at varied silica-to-alumina ratios. It is a preferred embodiment of the present invention that the mordenite be of the hydrogen form and that the silica-toalumina ratio be at least 16:1, more specifically, in the range from 16:1 to 60:1. The pretreatment steps taught in the aforementioned references are routinely and typically employed in the manufacture of commercially available mordenite powders which meet the requirements as a starting material as set forth in the present invention. These pretreatment steps are used to increase the silica-toalumina ratio of the mordenite zeolite and to convert the sodium form to the more desirable hydrogen form.

To manufacture the transalkylation catalyst of the instant process, hydrogen form mordenite is incorporated with alumina and formed into a catalytic composite. The formed catalytic composite may be prepared by any known method in the art including the well-known oil drop and extrusion methods. The hydrogen form mordenite may be present in an amount within the range of 50 to about 99.5 wt. %, preferably within the commercially desirable range of 75 to about 95 wt. %. Thus, the alumina is preferably present in an amount within the range of from about 5 to about 25 wt. %, based on total weight of the catalyst composition.

The preferred alumina for use in the present invention is selected from the group consisting of gamma-alumina, eta-alumina, and mixtures thereof. Most preferred is gamma-alumina. Other refractory inorganic oxides which may be used include, for example, silica gel, silica-alumina, magnesia-alumina, zirconia-alumina, phosphorus-containing alumina, and the like.

Surprisingly and unexpectedly, it has been found that a catalyst composition prepared in accordance with and containing the components as claimed in the invention will possess a surface area higher than any catalyst heretofore described in the art. This high surface area of at least 580 $m^2/g$ is surprising when one considers not only the diluting affect of an alumina support material having relatively low surface area (maximum approximately 250 $m^2/g$), but also considering the lowering of surface area caused by the particular forming technique employed. Catalysts of the prior art do not obtain the high surface area of the instant catalyst and thus demonstrate inferior performance, particularly as alkylation and transalkylation catalysts. The prior art does not teach or suggest how to obtain a mordenite/alumina catalyst having a surface area of at least 580 $m^2/g$. Surface area, as referred to herein, is determined by employing the Langmuir method of correlating adsorption/desorption isotherm data. The Langmuir method is especially suitable for catalytic composites containing high percentages of crystalline aluminosilicates. The data needed for the Langmuir method is typically obtained by well-known adsorption/ desorption apparatuses, preferably a nitrogen adsorption/desorption apparatus. Therefore, the present process allows for a transalkylation catalyst composition using a high surface area mordenite without loss of this surface area when formed with alumina to give a commercially acceptable formulation. Likewise, the benefit of the presence of alumina, which imparts, among other things, strength to the catalyst composition, may be achieved without penalty with regard to the surface area of the mordenite.

Any method may be employed which results in a final transalkylation catalyst composite having at least a surface area of 580 $m^2/g$. Catalyst compositions with high surface areas can be arrived at in a number of ways, such as, using a hydrogen form mordenite powder which inherently has a very high surface area, or by having one component of the composite, which has a high surface area, in great proportion to other components. A preferred method of achieving a surface area of at least 580 m$^2$/g is to contact the formed catalytic composite with an acidic aqueous solution. This acidic aqueous solution may contain ammonium ions. The formed catalyst composite may be dried and/or calcined prior to its contact with the aqueous solution.

The acidic nature of the aqueous solution is attained by employing an acid. Particularly suitable are strong mineral acids such as $H_3PO_4$, $H_2SO_4$, $HNO_3$, and HCl. HCl is the preferred acid of the present invention. Of course, it is contemplated that mixtures of various acids may also be employed. If the acidic aqueous solution contains ammonium ions, the preferred source of these ions is $NH_4Cl$, but any ammonium compound which can form ammonium ions, such as $NH_4OH$, $NH_4NO_3$, $NH_4$ sulfate, $NH_4$ phosphates, and the like, should be suitable.

Concentrations of the acid and ammonium ions in the aqueous solution are not critical and can vary from 0.5M to 6M for the acid concentration and 0.5M to 4M for the ammonium ion concentration. Particularly good results are obtained using a solution containing acid and ammonium ion concentrations within the range of 2 to 5M for the acid and 1 to 3M for the ammonium ion.

A plurality of methods for contacting the formed catalytic composite and the acidic aqueous solution is envisioned with no one method of particular advantage. Such contacting methods may include, for example, a stationary catalyst bed in a static solution, a stationary catalyst bed in an agitated solution, a stationary catalyst bed in a continuously flowing solution, or any other means which efficiently contacts the catalyst composition with the acidic aqueous solution.

The temperature of the contacting solution should be within the range of 25° to about 100° C., preferably within the range of from about 50° to about 98° C. The time required for the contacting step will depend upon concentrations, temperature, and contacting efficiency. In general, the contacting time should be at least 0.5 hour, but not more than 4 hours, preferably between 1 and 3 hours in duration.

As a result of contacting the formed catalytic composite with the acidic aqueous solution, an increase in the measured surface area is observed. Surprisingly and unexpectedly, this increase in surface area, to 580 m$^2$/g or higher, is not accompanied by an increase in the silica-to-alumina ratio of the hydrogen form crystalline aluminosilicate as measured by Magic Angle Spinning NMR (MASNMR). The MASNMR technique, which is a well-known analytical method of the art, indicates no reduction in the framework tetrahedral aluminum atoms of catalyst compositions of the present invention. Although it is not certain the exact reason why the surface area is higher after contacting the formed catalytic composite, it is believed that the acidic aqueous solution is removing occluded ions from the mordenite which are deposited therein as a result of the forming technique employed. The catalyst of the instant invention has particular utility in the alkylation or transalkylation of aromatic hydrocarbons.

In a continuous process comprising in part a transalkylation zone for the transalkylation of polyalkylaromatic compounds with an aromatic substrate, the above-described transalkylation reactants are fed in admixture into a pressure vessel containing the above-described acid-washed crystalline silicaalumina transalkylation catalyst. The transalkylation catalyst may be contained in one bed within a reactor vessel or divided up among a plurality of beds within a reactor. The transalkylation reaction system may contain one or more reaction vessels in series. The feed to the transalkylation reaction zone can flow vertically upwards, or downwards through the catalyst bed in a typical plug-flow reactor, or horizontally across the catalyst bed in a radial flow type reactor.

Temperatures which are suitable for use in the process herein are those temperatures which initiate a reaction between an aromatic substrate compound and the polyalkylaromatic compounds recovered in the separations section to selectively produce the desired monoalkylaromatic compound. Generally, temperatures suitable for promoting the transalkylation reactions are from about 100° C. to about 390° C., and especially from about 125° C. to about 275° C. Pressures which are suitable for use herein preferably are above about 1 atm but should not be in excess of about 130 atm. An especially desirable pressure range is from about 10 to about 40 atm. A liquid hourly space velocity (LHSV) of from about 0.1 to about 50 hr$^{-1}$, and especially from about 0.5 to about 5 hr$^{-1}$ based upon the combined aromatic substrate and polyalkylaromatic feed rate is desirable. It should be noted that the temperature and pressure combination utilized in the transalkylation reaction zone is to be such that the transalkylation reactions take place in essentially the liquid phase. In a liquid phase transalkylation process for producing monoalkylaromatics, the catalyst is continuously washed with reactants, thus preventing buildup of coke precursors on the catalyst. This results in reduced amounts of carbon forming on said catalyst in which case catalyst cycle life is extended as compared to a gas phase transalkylation process in which coke formation and catalyst deactivation is a major problem. Additionally, the selectivity to monoalkylaromatic production, especially cumene production, is higher in the catalytic liquid phase transalkylation reaction herein as compared to catalytic gas phase transalkylation reaction.

Figure 3:
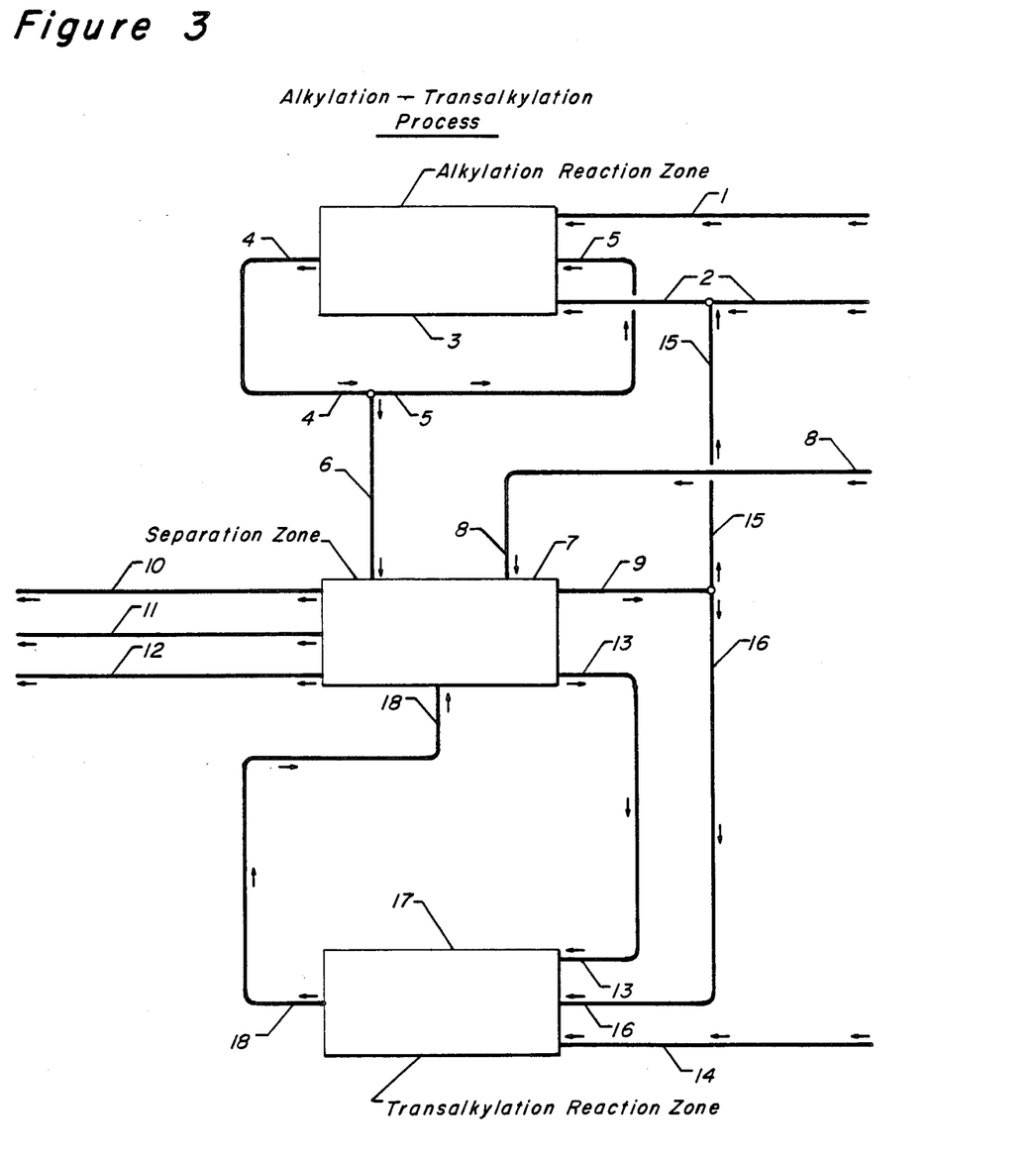
FIG. 3 is a basic flow diagram of the process of the instant invention.

Understanding of this invention will be facilitated by reference to FIG. 3 which is a diagram of the process flow scheme of the instant invention. As stated hereinabove, the first step of the process of the present invention comprises passing into an alkylation reaction zone 3 containing an alkylation catalyst, an aromatic substrate feed stream 2, and an alkylating agent feed stream 1. A portion of the alkylation reaction zone effluent stream 4 may be introduced into the inlet of the alkylation reaction zone via line 5. The remaining portion of the alkylation reaction zone product stream 4 is sent to the separations zone 7 via line 6.

The separations zone 7 accepts as feed a portion to all of the alkylation reaction zone product stream via line 6 and the entire transalkylation reaction zone product stream via line 18. In addition, a portion to all of the aromatic substrate used as alkylation and transalkylation reaction zone feed may be initially introduced into the separations zone 7 via line 8 for purification of the aromatic substrate feed. The separations zone 7 produces three product streams 10, 11, and 12 and two recycle streams 9 and 13. The products separated in the separations zone 7 include the desired monoalkylaromatic stream 10, a heavy by-product stream 11, and a light by-product stream 12. The recycle stream components recovered in the separations zone are an aromatic substrate stream 9 which can be employed as a portion to all of the aromatic substrate feed 2 to the alkylation reaction zone via line 15. Additionally, the recovered aromatic substrate stream 9 can be used as a portion to all of the transalkylation reaction zone 17 aromatic substrate feed via line 16. Polyalkylated aromatics are recovered as a recycle stream in the separations zone 7 and sent in entirety via line 13 to the transalkylation reaction zone 17 as a portion of the transalkylation reaction zone feed.

The transalkylation reaction zone 17 accepts as feed the polyalkylated compounds recovered in the separations zone 7 and supplied to the transalkylation reaction zone 7 via line 13. An aromatic substrate utilized as an alkylation reaction zone feedstock is also employed as a transalkylation reaction zone 17 feedstock. The aromatic substrate can be supplied directly to the reactor from a source outside of the process via line 14, as a recycle stream of aromatic substrate recovered in the separations zone via line 16 or as a mixture of both.

BRIEF DESCRIPTION OF THE DRAWINGS

FIG. 1 is a graph of the diisopropylbenzene (DIPB) conversion in percent expressed alternatively as:

$$\left(1 - \frac{\text{moles DIPB in feed}}{\text{moles DIPB in product}}\right) \times 100$$

plotted against hours on stream.

FIG. 2 is a plot of benzene conversion in percent plotted against hours on stream where benzene conversion may be expressed as:

$$\left(1 - \frac{\text{moles benzene in feed}}{\text{moles benzene in product}}\right) \times 100.$$

EXAMPLE I

A number of experiments were undertaken to study the performance of various catalytic composites in an alkylation reaction system and in a transalkylation reaction system. Overall, five different catalyst formulations were tested for their utility in promoting alkylation and/or transalkylation reactions.

Catalyst A is a solid phosphoric acid catalyst. It has been sized to pass through a 20 mesh screen and be retained on a 40 mesh screen. The catalyst is composed of phosphoric acid on kieselguhr, of which about 26 wt. % is phosphorus. This catalyst does not conform to either the alkylation or transalkylation catalyst of the present invention, however it is a commonly used alkylation catalyst.

EXAMPLE II

Catalyst B is the alkylation reaction zone catalyst of the present invention. Catalyst B was prepared in accordance with the cogelled, spherical alkylation reaction zone catalyst formulation of the present invention. Catalyst B is characterized in that it has a 75:25 silica-to-alumina ratio.

EXAMPLE III

Catalyst C was formulated by a method inconsistent with that of the alkylation or transalkylation catalyst of the present invention. The starting material for catalyst C was the hydrogen form, low sodium, partially dealuminated synthetic mordenite powder (marketed by Union Carbide under the name LZ-M-8), hereinafter referred to as the as-received mordenite.

The as-received mordenite powder was mixed with an alumina powder to a weight ratio of 9:1, followed by the addition of an acidified peptization solution. The admixture was then extruded by means known in the art. After the extrusion process, the extrudate was dried and calcined. The resulting surface area of this catalyst was 540 m$^2$/g.

EXAMPLE IV

The catalyst base formulation used for Catalyst D is identical to that used for Catalyst C of Example III. The difference arises in the steps following the drying and calcination of the acid peptized silica/mordenite extrudate. Following the drying and calcination steps, the extrudate was exposed to an aqueous solution comprising 10 wt. % HCl and 10 wt. % NH$_4$Cl at 60° C. for 150 minutes at a solution to zeolite volumetric ratio of 5:1. After the acid wash step, the catalyst was again dried and calcined. Catalyst D is the acid-washed transalkylation reaction zone catalyst of the present invention. The resulting surface area of this catalyst was 620 m$^2$/g.

EXAMPLE V

Catalyst E was formulated by a method inconsistent with that of the alkyltion or transalkylation catalyst of the present invention. To prepare Catalyst E, a mixture of 50 wt. % mordenite powder and 50 wt. % alumina powder was combined with a 5.5 wt. % nitric acid solution. The resulting dough was extruded through a 1/16" die and sized at an L/D ratio of 2 to 5. The extrudate was calcined at 150° C. for 1 hour and then at 480° C. for 3 hours. The calcined extrudate was next contacted with a 15 wt. % solution of ammonia for 1 hour and then dried. The dried, finished extrudate was calcined at 150° C. for 1 our and 48° C. for 2 hours. Typical properties of the finished catalyst include a piece density of 1.23 and a surface area of 450 m$^2$/g.

EXAMPLE VI

Catalysts A, B, and D as described in the previous examples were evaluated for aromatic alkylation performance in a flow-through reactor containing 20 cc of catalyst by processing a feed comprising a mixture of benzene and propylene at a 4:1 molar ratio except for Catalyst A which had a ratio of 8:1. Conventional product recovery and analysis techniques were used to evaluate the catalyst performance in each case.

The operating conditions used to evaluate the alkylation performance of the three catalysts comprised a reactor pressure of 34 atmospheres, a liquid hourly space velocity of 4 hr$^{-1}$ based upon the benzene feed rate, and a maximum temperature of 200° C. No recycle of the reactor effluent to the reactor inlet was employed in this testing. The results of the pilot plant tests can be found in Table 1 below.

TABLE 1

| | Alkylation Reaction Selectivities | | |
|---|---|---|---|
| Yields (mole %) | Catalyst A 200° C. 8/1-BZ/C₃= | Catalyst B 200° C. | Catalyst D 200° C. |
| Cumene | 94.5 | 72.8 | 85.9 |
| Diisopropylbenzenes | 3.4 | 24.3 | 12.2 |
| -para | | 12.3 | 4.4 |
| -meta | | 10.0 | 7.7 |
| -ortho | | 1.1 | 0.1 |
| Triisopropylbenzene | | 2.9 | |
| Tetraisopropylbenzene | | 0.03 | |
| Total Isopropylbenzene | 97.9 | 99.1 | 98.1 |
| Non-Aromatics | 0.1 | 0.4 | 0.2 |
| N—Propylbenzene (ppm) | 150 | 190 | 6500 |
| Total Heavies | 2.0 | 0.5 | 0.9 |
| Bromine Index | 75 | <1 | <1 |

The pilot plant tests indicate that Catalyst B, the alkylation catalyst of the present invention produces an alkylation product which comprises 99.1 mole % isopropylbenzene compounds. The standard solid phosphoric acid catalyst (Catalyst A) produces only 97.9 mole % of isopropylbenzene compounds, while Catalyst D, the transalkylation catalyst of the present invention produces an alkylate with 98.1 mole % isopropylbenzene compounds. More importantly, Catalyst B, the noncrystalline silica-alumina catalyst of the present invention produces an alkylate product with only 0.5 mole % of materials other than polyisopropylbenzenes with a higher boiling point than cumene, and also produces a product with a bromine index of less than 1, and a product containing only 190 ppm normal propylbenzene. Catalyst A not of the present invention produces a product with a noraml propylbenzene content of only 150 ppm. However, the product produced by Catalyst A exhibits a bromine index of 75 and produces 2.0 mole % of useless heavy compounds. Catalyst D, the transalkylation catalyst of the present invention, produces a product with a bromine index of less than 1. However the alkylation reaction product produced by Catalyst D has an extremely high undesirable normal propylbenzene content of 6500 ppm.

Alkylation reaction test results indicate that Catalyst B, the noncrystalline silica-alumina alkylation catalyst of the present invention, produces an aromatic alkylate product that has levels of impurities including heavy compounds, normal propylbenzene, and olefin oligomers as measured by the bromine index that are surprisingly lower than the alkylation product of Catalyst A or the product of Catalyst D, the transalkylation catalyst of the present invention. These results also show that Catalyst B, the alkylation catalyst of the present invention, is superior to catalyst D, the transalkylation catalyst of the instant invention, in producing an alkylate product containing low amounts of impurities.

EXAMPLE VII

Figure 1:
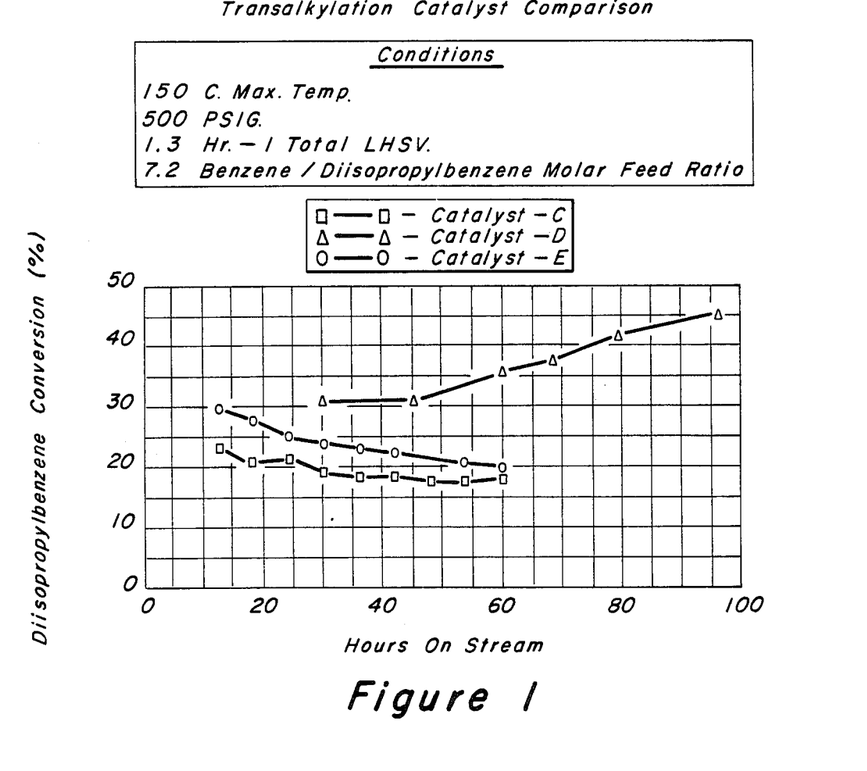
Figure 2:
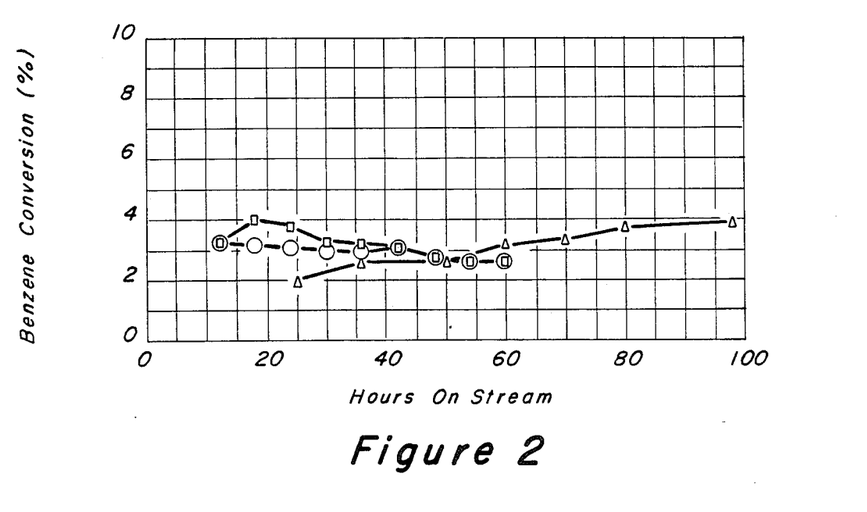

Catalyst D, the transalkylation catalyst of the present invention, was tested at transalkylation reaction conditions along with Catalysts C, a non-acid washed mordenite catalyst, and E, a low surface area mordenite catalyst, both not catalysts of the present invention. The catalysts were evaluated in a pilot plant consisting of a tubular reactor holding 50 cc of transalkylation catalyst and a product recovery zone. To the reactor was fed a liquid feed blend comprised of 7.2 moles of benzene, 1 mole of diisopropylbenzene, and 0.25 moles of other alkylbenzenes at a total liquid hourly space velocity (LHSV) of 1.3 hr$^{-1}$. The reactor pressure was operated at 34 atmospheres, and the reaction temperature was held at 150° C. maximum. The results of the pilot plant tests are presented in FIGS. 1 and 2. It is evident from FIG. 1 that the diisopropylbenzene conversion capability of Catalyst D, the transalkylation catalyst of the instant invention, is much higher than that of the two catalysts not of the instant invention. The ability of all three catalysts to promote the reaction of benzene with polyalkylated aromatics as seen in FIG. 2 is similar in all cases. This leads to the conclusion that Catalyst D, the acid-washed high surface area transalkylation catalyst of the instant invention, is more efficient in the transalkylation of diisopropylbenzene with benzene to produce cumene at a high diisopropylbenzene conversion than a non-acid washed or low surface area mordenite containing catalyst.

EXAMPLE VIII

The pilot plant results of the noncrystalline silica-alumina alkylation catalyst of the present invention and the acid-washed crystalline alumina-silica transalkylation catalyst of the present invention were combined in order to synthetically determine the yield of an alkylation/transalkylation process of the present invention. The following yield results are based upon an alkylation reaction zone benzene to propylene molar feed ratio of 4:1. Other alkylation reaction zone conditions include a temperature of 200° C., a pressure of 34 atm, and a liquid hourly space velocity of 4.0 hr$^{-1}$. The transalkylation reaction zone conditions the yield is based upon includes a temperature of 150° C., a pressure of 34 atm, a benzene to polyisopropyl benzene molar feed ratio of 7:1, and a liquid hourly space velocity of 1.3 hr$^{-1}$.

| | Metric Tons/Day |
|---|---|
| Alkylation Reaction Zone | |
| -Benzene Feed (Fresh) | 65 |
| -Benzene Feed (Recycle) | 229 |
| -Propylene Feed (Fresh) | 36 |
| -Reactor Effluent Recycle | 1162 |
| -Reactor Effluent to Separations Zone | 330 |
| Transalkylation Reaction Zone | |
| -Benzene Feed (Recycle) | 168 |
| -DIPB + TIPB Feed | 50 |
| Separations Zone Products | |
| -Cumene | 100 |
| -Heavy Products | 0.5 |
| -Light Products | 0.4 |
| -Recycle Benzene | 397 |
| -Recycle DIPB | 44 |
| -Recycle TIPB | 6 |

What is claimed is:

1. A process for the production of alkylated aromatics which comprises the steps of:
   (a) passing a feedstream comprising an alkylating agent and an aromatic substrate into an alkylation reaction zone containing an alkylation catalyst under conditions providing for the liquid phase alkylation of said aromatic substrate;
   (b) separating in a separations zone the product from the alkylation reaction zone and a hereinafter described transalkylation reaction zone product into fractions comprising (1) an aromatic substrate fraction, (2) a substantially pure monoalkylated aromatic fraction, and (3) a polyalkylated aromatic hydrocarbon fraction;

(c) passing a feed stream of an aromatic substrate and the separated polyalkylaromatic hydrocarbon fraction to a transalkylation reaction zone containing a catalytic composite comprising a hydrogen form mordenite dispersed in an alumina matrix, said composite comprising from about 5 to 25 wt. % of an inorganic oxide support and wherein said support is contacted with an acidic aqueous solution after it is formed, said contacting occurring at conditions selected to increase the surface area of the composite to at least 580 m$^2$/g without increasing the silica-to-alumina ratio of the mordenite at conditions sufficient for the transalkylation of said polyalkylaromatic hydrocarbon fraction to produce a transalkylation reaction zone product;

(d) introducing the transalkylation reaction zone product from step (c) into the separations zone of step (b); and (e) recovering the monooalkylaromatic fraction.

2. The process defined in claim 1 wherein at least a portion of the separated aromatic substrate fraction of step (b) is recycled to the alkylation reaction zone.

3. The process defined in claim 1 wherein at least a portion of the separated aromatic substrate fraction of step (b) is recycled to the transalkylation reaction zone.

4. The process defined in claim 1 wherein the alkylating agent is selected from the group consisting of an alkene, an alcohol, an alkylhalide, an alkylsulfonate, or mixtures thereof.

5. The process defined in claim 4 wherein the alkylating agent is a monoolefin and has a carbon number from 2 to 15.

6. The process defined in claim 1 wherein a portion of the alkylation reaction zone product is recycled to the inlet of the alkylation reactor.

7. A process for the liquid phase production of cumene which comprises the steps of:

(a) reacting propylene with benzene in the presence of a noncrystalline silica-alumina alkylation catalyst at liquid phase alkylation conditions in an alkylation reaction zone;

(b) dividing the liquid effluent of said alkylation reaction zone into at least two portions of like composition;

(c) recirculating a first divided portion of the liquid effluent to said alkylation reaction zone;

(d) passing a second divided portion of said alkylation reaction zone effluent stream and a transalkylation zone effluent as hereinafter characterized into a separations zone wherein entering hydrocarbons are separated into a benzene feed-rich fraction, a substantially pure cumene product fraction, and a polyisopropylbenzene fraction;

(e) transalkylating the polyisopropylbenzene fraction with a first portion of the separated benzene-rich feed fraction in a transalkylation reaction zone in the presence of a transalkylation catalyst comprising about 75 to 95 wt. % of a hydrogen form mordenite dispersed in about 5 to 25 wt. % of an inorganic oxide support, the alkylation catalyst prepared by forming said support, and contacting said formed support with an acidic aqueous solution under conditions selected to increase the surface area of the composite to at least 580 m$^2$/g without increasing the silica-to-alumina ratio of the mordenite, the reaction zone operates at transalkylation reaction conditions to produce a transalkylation reactin zone effluent stream;

(f) supplying the effluent of the transalkylation reaction zone to said separations zone as said transalkylation reaction zone effluent stream;

(g) recirculating a second portion of said unreacted benzene-rich feed fraction to said alkylation reaction zone as a portion of the alkylation reaction zone feed; and (h) recovering said cumene product fraction from the separations zone.

8. The process defined in claim 7 wherein the transalkylation reaction zone catalyst is comprised of from 5 to 25 wt. % of an inorganic oxide support selected from the group consisting of Al2O3, SiO2, AlPO4, and mixtures thereof.

9. The process defined in claim 8 wherein the transalkylation reaction zone catalyst has been treated by contacting it with a 0.01 to 20 wt. % solution of a mineral or organic acid for 1 minute to 24 hours or longer.

10. The process defined in claim 7 wherein the alkylation reaction zone catalyst is a noncrystalline silica-alumina material with a silica-to-alumina ratio of from 2:3 to 99:1.

11. A process for the liquid phase production of cumene which comprises the steps of:

(a) reacting propylene with benzene in the presence of a noncrystalline silica-alumina alkylation reaction zone catalyst with a silica-to-alumina ratio of from 2:3 to 99:1 at a temperature of from 100° to 390° C., a pressure of from 1 to 130 atmospheres, a liquid hourly space velocity of from 0.5 to 50 hr$^{-1}$, and a benzene-to-propylene molar feed ratio of from 1:1 to 20:1 in an alkylation reaction zone;

(b) dividing the liquid effluent of said alkylation reaction zone into at least two portions of like composition;

(c) recirculating a first divided portion of the alkylation reaction zone liquid effluent to said alkylation reaction zone;

(d) passing a second divided portion of said alkylation reaction zone effluent and a transalkylation reaction zone effluent stream as hereinafter characterized into a separations zone wherein entering hydrocarbons are separated into a benzene feed-rich fraction, a substantially pure cumene product fraction, and a polyisopropylbenzene fraction;

(e) transalkylating the polyisopropylbenzene fraction with a first portion of the separated benzene-rich feed fraction in the presence of a transalkylation reaction zone catalyst comprising from 5 to 95 wt. % of mordenite, from 5 to 95 wt. % of Al2O3, wherein the transalkylation reaction zone catalyst has been contacted with a 0.01 to 20 wt. % solution of HCl for 1 minute to 24 hours or longer at a transalkylation reaction zone temperature of from 100° C. to 390° C., a pressure of from 1 to 130 atmospheres, a liquid hourly space velocity of from 0.1 to 50 hr$^{-1}$ and a benzene to polyisopropylbenzene molar feed ratio of from 1:1 to 1:20 to produce a transalkylation reaction zone effluent stream;

(f) supplying the effluent of the transalkylation reaction zone to said separations zone as said transalkylation reaction zone effluent stream;

(g) recirculating a second portion of said unreacted benzene-rich feed fraction to said alkylation reaction zone as a portion of the alkylation reaction zone feed; and (h) recovering said cumene product fraction from the separations zone.

12. The process defined in claim 11 wherein the alkylation reaction zone or transalkylation reaction zone catalyst can be in the form of spheres, extrudates, or granular particles.

13. The process defined in claim 11 wherein the treated transalkylation reaction zone catalyst has a surface area greater than about 580 m²/g.

14. The process defined in claim 13 wherein the benzene feed stream is introduced into the separations zone.

15. The process defined in claim 14 wherein the alkylation reaction zone feed is saturated with $H_2$.

16. The process defined in claim 15 wherein the transalkylation reaction zone feed is saturated with $H_2$.

17. The process defined in claim 16 wherein a portion of the first divided portion of the alkylation reaction zone effluent stream is used for quenching the alkylation reaction.

* * * * *